(12) United States Patent
Ylitalo et al.

(10) Patent No.: US 7,807,661 B2
(45) Date of Patent: Oct. 5, 2010

(54) SILVER ION RELEASING ARTICLES AND METHODS OF MANUFACTURE

(75) Inventors: Caroline M. Ylitalo, Stillwater, MN (US); Linda K. M. Olson, St. Paul, MN (US); Hassan Sahouani, Hastings, MN (US); Kim M. Vogel, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 117 days.

(21) Appl. No.: 11/275,075

(22) Filed: Dec. 8, 2005

(65) Prior Publication Data

US 2007/0134301 A1    Jun. 14, 2007

(51) Int. Cl.
    *A01N 43/68* (2006.01)
(52) U.S. Cl. ........................................ 514/183; 514/245
(58) Field of Classification Search ........................ None
    See application file for complete search history.

(56) References Cited

U.S. PATENT DOCUMENTS

| | | | |
|---|---|---|---|
| 4,689,338 A | 8/1987 | Gerster |
| 4,882,166 A | 11/1989 | Graham et al. |
| 4,929,624 A | 5/1990 | Gerster et al. |
| 4,988,815 A | 1/1991 | André et al. |
| 5,037,986 A | 8/1991 | Gerster |
| 5,175,296 A | 12/1992 | Gerster |
| 5,837,275 A | 11/1998 | Burrell et al. |
| 5,876,682 A | 3/1999 | Kurihara et al. |
| 5,948,487 A | 9/1999 | Sahouani et al. |
| 6,051,290 A | 4/2000 | Sahouani et al. |
| 6,069,149 A | 5/2000 | Nanba et al. |
| 6,214,499 B1 | 4/2001 | Helber et al. |
| 6,245,399 B1 | 6/2001 | Sahouani et al. |
| 6,248,364 B1 | 6/2001 | Sengupta et al. |
| 6,344,272 B1 | 2/2002 | Oldenburg et al. |
| 6,355,386 B1 | 3/2002 | Helber et al. |
| 6,395,354 B1 | 5/2002 | Sahouani et al. |
| 6,411,354 B1 | 6/2002 | Lavrentovich et al. |
| 6,488,866 B1 | 12/2002 | Sahouani et al. |
| 6,527,977 B2 | 3/2003 | Helber et al. |
| 6,538,714 B1 | 3/2003 | Sahouani et al. |
| 6,562,363 B1 | 5/2003 | Mantelle et al. |
| 6,570,632 B2 | 5/2003 | Lavrentovich et al. |
| 6,574,044 B1 | 6/2003 | Sahouani et al. |
| 6,576,712 B2 | 6/2003 | Feldstein et al. |
| 6,645,578 B2 | 11/2003 | Sahouani et al. |
| 6,673,398 B2 | 1/2004 | Schneider et al. |
| 6,696,077 B2 | 2/2004 | Scherr |
| 6,699,533 B2 | 3/2004 | Sahouani et al. |
| 6,777,036 B2 | 8/2004 | Bravo Vasquez et al. |
| 6,962,734 B2 | 11/2005 | Nazarov et al. |
| 2002/0055517 A1 | 5/2002 | Smith |
| 2002/0066885 A1 | 6/2002 | Sahouani et al. |
| 2002/0132065 A1 | 9/2002 | Sahouani et al. |
| 2002/0168511 A1 | 11/2002 | Schneider et al. |
| 2003/0008145 A1 | 1/2003 | Goldstein |
| 2003/0071243 A1 | 4/2003 | Sahouani et al. |
| 2003/0147043 A1 | 8/2003 | Sahouani et al. |
| 2004/0058091 A1 | 3/2004 | Dutova et al. |
| 2004/0242729 A1 | 12/2004 | Baran, Jr. et al. |
| 2005/0123621 A1 | 6/2005 | Burton et al. |
| 2005/0124724 A1 | 6/2005 | Burton et al. |
| 2006/0035039 A1 | 2/2006 | Ylitalo et al. |
| 2006/0110528 A1 | 5/2006 | Sahouani |
| 2006/0110540 A1 | 5/2006 | Sahouani |
| 2006/0110922 A1 | 5/2006 | Sahouani |
| 2006/0111482 A1 | 5/2006 | Sahouani |
| 2007/0086964 A1 | 4/2007 | Moran et al. |
| 2007/0086965 A1 | 4/2007 | Mohanty et al. |
| 2007/0128291 A1 | 6/2007 | Tokie et al. |
| 2007/0140957 A1 | 6/2007 | Mohanty et al. |
| 2007/0141351 A1 | 6/2007 | Mohanty et al. |
| 2007/0148458 A1 | 6/2007 | Sahouani et al. |
| 2007/0243258 A1 | 10/2007 | Choban |
| 2007/0275185 A1 | 11/2007 | Sahouani et al. |

FOREIGN PATENT DOCUMENTS

| | | |
|---|---|---|
| EP | 1 232 414 B1 | 2/2004 |
| KR | 10-2003-0010846 | 2/2003 |
| KR | 10-2005-0023294 | 3/2005 |
| WO | WO 98/37997 A2 | 9/1998 |
| WO | WO 00/22463 A1 | 4/2000 |
| WO | WO 01/80920 A2 | 11/2001 |
| WO | WO 02/18003 A1 | 3/2002 |
| WO | 2004/033488 A2 | 4/2004 |
| WO | WO 2005/011629 A1 | 2/2005 |

(Continued)

OTHER PUBLICATIONS

Aguirre, et al., "CTAB Mediated Reshaping of Metallodielectric Nanoparticles", Nano Letters, (2003), pp. 1707-1711, vol. 3, No. 12, American Chemical Society.

(Continued)

*Primary Examiner*—Brandon J Fetterolf
*Assistant Examiner*—Timothy P Thomas
(74) *Attorney, Agent, or Firm*—Gregory D. Allen

(57) ABSTRACT

A biologically-active article includes a substrate having a substrate surface and a silver releasing chromonic material disposed adjacent to the substrate surface. The silver releasing chromonic material includes a chromonic compound and a silver ion source. Methods of forming the same are also disclosed.

13 Claims, 1 Drawing Sheet

FOREIGN PATENT DOCUMENTS

| WO | WO 2005/012488 A2 | 2/2005 |
|---|---|---|
| WO | WO 2006/020584 A2 | 2/2006 |
| WO | WO 2007/067535 | 6/2007 |

OTHER PUBLICATIONS

Barbic et al., "Single Crystal Silver Nanowires Prepared by the Metal Amplification Method", Journal of Applied Physics, (Jun. 1, 2002), pp. 9341-9345, vol. 91, No. 11, 2002 American Institute of Physics.

Ding et al., "Structure Analysis of Nanowires and Nanobelts by Transmission Electron Microscopy", J. Phys. Chem. B, (2004), pp. 12280-12291, vol. 108, No. 33.

Hong et al., "Ultrathin Single-Crystalline Silver Nanowire Arrays Formed in an Ambient Solution Phase", Science, (Oct. 12, 2001), pp. 348-351, vol. 294.

Hurley, L. H. et al., "G-quadruplexes as Targets for Drug Design", *Pharmacol Ther.*, (Mar. 2000), vol. 83, No. 3, pp. 141-158.

Kostko, A. F. et al., "Salt Effects on the Phase Behavior, Structure, and Rheology of Chromonic Liquid Crystals", *J. Phys. Chem.*, (Oct. 20, 2005), vol. 109, No. 41, pp. 19126-19133.

Kumar et al., "Linear Superclusters of Colloidal Gold Particles by Electrostatic Assembly on DNA Templates", Advanced Materials, (Mar. 2, 2001), pp. 341-344, vol. 13, No. 5, Wiley-VCH Verlag GmbH, D-69469 Weinheim.

Medintz et al., "Self-Assembled Nanoscale Biosensors Based on Quantum Dot FRET Donors", Nature Materials, (Sep. 2003), pp. 630-638, vol. 2, Nature Publishing Group.

Zhang et al., "Polymer Microgels: Reactors for Semiconductor, Metal, and Magnetic Nanoparticles", JACS, (2004), 7908-7914, vol. 126, No. 25, American Chemical Society.

Fang et al., "Aggregation and Surface-Enhanced Raman Activity Study of Dye-Coated Mixed Silver-Gold Colloids", Journal of Raman Spectroscopy, (2004), pp. 914-920, vol. 35, No. 11, John Wiley & Sons, Ltd.

Stenzel et al., "The Incorporation of Metal Clusters Into Thin Organic Dye Layers as a Method for Producing Strongly Absorbing Composite Layers: An Oscillator Model Approach to Resonant Metal Cluster Absorption", Journal of Physics D: Applied Physics, (1995), pp. 2154-2162, vol. 28, No. 10, IOP Publishing, Ltd.

Huang et al., "Nanowire Arrays Electrodeposited from Liquid Crystalline Phases", Advanced Materials, (Jan. 4, 2002), pp. 61-64, vol. 14, No. 1, Wiley-VCH Verlag GmbH, D-69469 Weinheim.

Attwood et al., "Lyotropic Mesophase Formation by Anti-Asthmatic Drugs", Mol. Cryst. Liq. Cryst., (1984), pp. 349-357, vol. 108.

Brinker et al., "Review of Sol-Gel Thin Film Formation", Journal of Non-Crystalline Solids, (1992), pp. 424-436, vol. 147&148, Elsevier Science Publishers B.V.

Kawasaki et al., "Controlled Layering of Two-Dimensional J-Aggregate of Anionic Cyanine Dye on Self-Assembled Cysteamine Monolayer on Au(111)", Langmuir, (2000), pp. 5409-5417, vol. 16, No. 12, American Chemical Society.

Lydon, "Chromonic Mesophases", Current Opinion in Colloid and Interface Science, (2004), pp. 480-490, vol. 8, Elsevier Ltd.

Lydon, "Chapter XVIII, Chromonics", Handbook of Liquid Crystals, (1998), pp. 981-1007, vol. 2 B: Low Molecular Weight Liquid Crystals II, Wiley-VCH Verlag GmbH, D-60469, Weinheim.

Lansdown, "Silver 1: Its Antibacterial Properties and Mechanism of Action", Journal of Wound Care, (Apr. 2002), pp. 125-130, vol. 11, No. 4.

Lansdown, "Silver 2: Toxicity in Mammals and How its Products Aid Wound Repair", Journal of Wound Care, (May 2002), pp. 173-177, vol. 11, No. 5.

Pardavi-Horvath, "Iron-Alumina Nanocomposites Prepared by Ball Milling", IEEE Transactions on Magnetics, (Sep. 1992), pp. 3186-3188, vol. 28, No. 5.

Wright et al., "Wound Management in an Era of Increasing Bacterial Antibiotic Resistance: A Role for Topical Silver Treatment", AJIC, (Dec. 1998), pp. 572-577, vol. 26, No. 6, Association for Professionals in Infection Control and Epidemiology, Inc.

PCT International Search Report for PCT/US2006/046387, Mailing Date: Apr. 20, 2007.

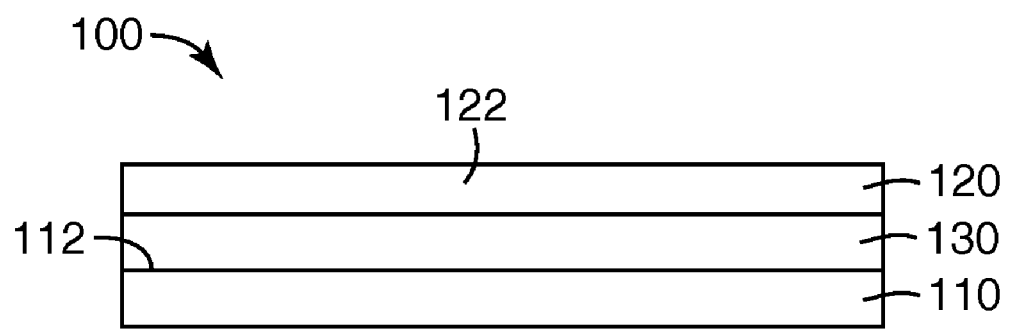

US 7,807,661 B2

SILVER ION RELEASING ARTICLES AND METHODS OF MANUFACTURE

BACKGROUND

The present disclosure relates to silver ion-releasing articles. More specifically the present disclosure relates to silver ion releasing chromonic articles and methods of making the same.

Silver is known for its antimicrobial activity. The Greeks and the Romans used silver lined water vessels to purify water. Silver nitrate was used over 100 years ago as an antimicrobial treatment for burn wounds. In the 1960's silver sulfadiazine cream replaced silver nitrate as an antimicrobial treatment for burn wounds. It is believed that the antimicrobial action of silver is due at least in part, to free silver ions or radicals, where the silver ions kill microbes by blocking the cell respiration pathway, by attaching to the cell DNA and preventing its replication, and by disruption of the cell membrane.

It is believed that wounds heal better in a moist environment. However, keeping wounds moist can cause bacterial proliferation in the wound bed. One way to combat wound infection is through the use of antibiotics. However, the systematic use of antibiotics to prevent wound infection is discouraged due to concerns of the generation of antibiotic resistant bacteria. Many silver compounds, such as silver nitrate, are very soluble in a moist environment and oxidize rapidly, thereby staining skin and providing only short term antimicrobial activity. There is a need for a broad-spectrum sustained release antimicrobial wound dressing for the treatment of chronic wounds.

SUMMARY

The present disclosure provides silver releasing articles and specifically silver ion releasing chromonic articles and methods of making the same. In some embodiments, these silver ion releasing chromonic articles provide time dependent controlled release of silver ions, even under moist conditions.

One aspect of the present disclosure relates to a biologically-active article that includes a substrate having a substrate surface and a silver releasing chromonic material disposed adjacent to the substrate surface. The silver releasing chromonic material includes a chromonic compound and a silver ion source.

In another aspect of the present disclosure, methods of forming silver releasing articles are described. These methods include, providing a substrate having a substrate surface, combining a silver salt with a chromonic compound in an aqueous solution to form an aqueous silver chromonic solution, disposing the silver chromonic solution adjacent to the substrate surface to form a coated substrate, and removing water from the coated substrate to form a silver ion releasing chromonic layer.

The above summary is not intended to describe each disclosed embodiment or every implementation of the present disclosure. The Figures, Detailed Description and Examples that follow more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 1 is a schematic cross-sectional view of an illustrative wound dressing article.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure provides silver releasing articles and specifically silver ion releasing chromonic articles and methods of making the same. In some embodiments, these silver ion releasing chromonic articles provide time dependent controlled release of silver ions, even under moist conditions.

For the following defined terms, these definitions shall be applied, unless a different definition is given in the claims or elsewhere in this specification.

Weight percent, percent by weight, % by weight, % wt, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, reference to a composition containing "a layer" includes of two or more layers. As used in this specification and the appended claims, the term "or" is generally employed in its sense including "and/or" unless the content clearly dictates otherwise.

Unless otherwise indicated, all numbers expressing quantities of ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The term, "chromonic materials" (or "chromonic compounds") refers to large, multi-ring molecules typically characterized by the presence of a hydrophobic core surrounded by various hydrophilic groups (see, for example, Attwood, T. K., and Lydon, J. E., Molec. Crystals Liq. Crystals, 108, 349 (1984)). The hydrophobic core can contain aromatic and/or non-aromatic rings. When in solution, these chromonic materials tend to aggregate into a nematic ordering characterized by a long-range order. Chromonic materials are capable of forming a chromonic phase or assembly when dissolved in an aqueous solution (preferably, an alkaline aqueous solution). Chromonic phases or assemblies are known and consist of stacks of flat, multi-ring aromatic molecules. The molecules consist of a hydrophobic core surrounded by hydrophilic groups. The stacking can take on a number of morphologies, but is typically characterized by a tendency to form columns created by a stack of layers. Ordered stacks of molecules are formed that grow with increasing concentration.

The unique stacking structure of the chromonics molecules allows for the stabilization of silver ions in an aqueous solution. These solutions can be delivered by a wide range of methods including coating, dipping, and non-contact deposition methods such as spraying and inkjet printing. In addition, the chromonic molecules can control the rate of antimicrobial silver ion release into a wound, thus providing sustained silver ion release.

FIG. 1 is a schematic cross-sectional view of an illustrative wound dressing article 100. The depicted layers are not to scale. This article 100 includes a substrate 110 having a substrate surface 112 and a silver ion releasing chromonic material 120 disposed adjacent to the substrate surface 112. The silver ion releasing chromonic material 120 includes a chromonic compound and a silver ion source 122. In some embodiments, an adhesive layer 130 is disposed between the substrate 110 and the silver ion releasing chromonic material 120.

Chromonic material is utilized to encapsulate a silver ion source and provide controlled release of silver ions from the chromonic structure. In many embodiments, a release of silver ions is triggered and controlled by exposing the chromonic structure to moisture. While not wishing to be bound by any particular theory, it is believed that the flat aromatic structure of the chromonic molecules results in self-assembling structures, which associate linearly and stack in a direction orthogonal to their linear association direction. These associations can result in rows of cavities into which silver ion sources can intercalate.

The silver ion releasing chromonic material 120 can be formed in any useful manner. In many embodiments, a silver ion source and the chromonic compound are combined in an aqueous solution to form silver ion releasing chromonic materials. These silver ion releasing chromonic materials can be represented by one of the following general structures:

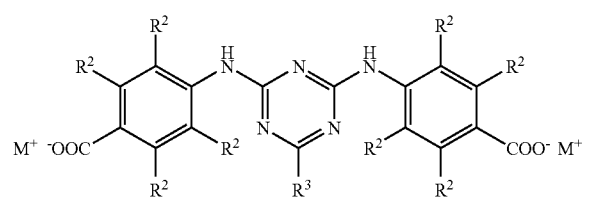

(I)

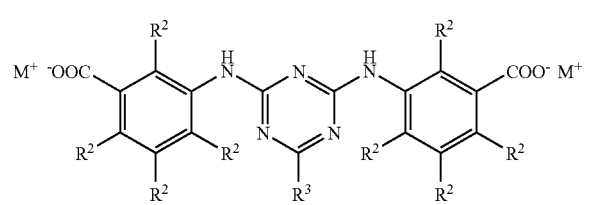

(II)

where; each $R^2$ is independently selected from the group consisting of electron donating groups, electron withdrawing groups, and electron neutral groups; $R^3$ is selected from the group consisting of substituted and unsubstituted heteroaromatic rings and substituted and unsubstituted heterocyclic rings, these rings being linked to the triazine group through a nitrogen atom within the ring of $R^3$, and $M^+$ is a silver metal cation. Preferably $R^3$ is selected from the group consisting of substituted and unsubstituted heteroaromatic rings.

The general structures above show orientations in which the carboxy group is para with respect to the amino linkage to the triazine backbone of the compound (formula I) and in which the carboxy group is meta with respect to the amino linkage to the triazine backbone (formula II). The carboxy group can also be a combination of para and meta orientations (not shown). In some embodiments, the orientation is para.

In many embodiments, each $R^2$ is hydrogen or a substituted or unsubstituted alkyl group. In some embodiments, $R^2$ is independently selected from the group consisting of hydrogen, unsubstituted alkyl groups, alkyl groups substituted with a hydroxy or halide functional group, and alkyl groups comprising an ether, ester, or sulfonyl. In one embodiment, $R^2$ is hydrogen.

$R^3$ can be, but is not limited to, heteroaromatic rings derived from pyridine, pyridazine, pyrimidine, pyrazine, imidazole, oxazole, isoxazole thiazole, oxadiazole, thiadiazole, pyrazole, triazole, triazine, quinoline, and isoquinoline. In many embodiments, $R^3$ includes a heteroaromatic ring derived from pyridine or imidazole. A substituent for the heteroaromatic ring $R^3$ can be selected from, but is not limited to, the group consisting of substituted and unsubstituted alkyl, carboxy, amino, alkoxy, thio, cyano, amide, sulfonyl, hydroxy, halide, perfluoroalkyl, aryl, ether, and ester. In some embodiments, the substituent for $R^3$ is selected from the group consisting of alkyl, sulfonyl, carboxy, halide, perfluoroalkyl, aryl, ether, and alkyl substituted with hydroxy, sulfonyl, carboxy, halide, perfluoroalkyl, aryl, or ether. When $R^3$ is a substituted pyridine, the substituent is preferably located at the 4-position. When $R^3$ is a substituted imidazole, the substituent is preferably located at the 3-position.

Representative examples of $R^3$ include 4-(dimethylamino)pyridinium-1-yl, 3-methylimidazolium-1-yl, 4-(pyrrolidin-1-yl)pyridinium-1-yl, 4-isopropylpyridinium-1-yl, 4-[(2-hydroxyethyl)methylamino]pyridinium-1-yl, 4-(3-hydroxypropyl)pyridinium-1-yl, 4-methylpyridinium-1-yl, quinolinium-1-yl, 4-tert-butylpyridinium-1-yl, and 4-(2-sulfoethyl)pyridinium-1-yl, shown below.

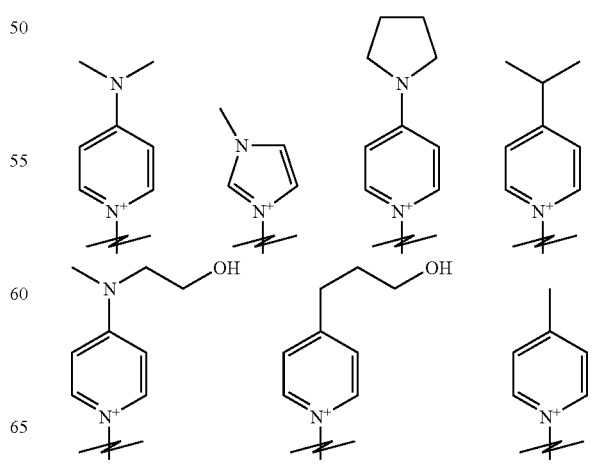

-continued

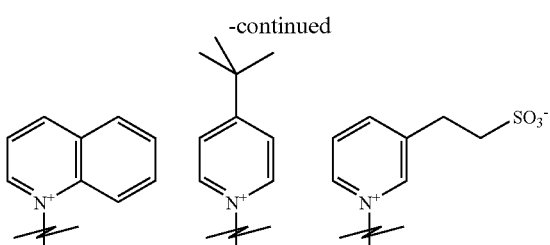

$R^3$ can also be represented by the following general structure:

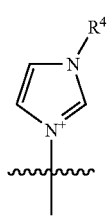

wherein $R^4$ is hydrogen or a substituted or unsubstituted alkyl group. In many embodiments, $R^4$ is selected from the group consisting of hydrogen, unsubstituted alkyl groups, and alkyl groups substituted with a hydroxy, ether, ester, sulfonate, or halide functional group. In many embodiments, $R^4$ is selected from the group consisting of propyl sulfonic acid, methyl, and oleyl.

$R^3$ can also be selected from N-substituted heterocyclic rings such as, for example, morpholine, pyrrolidine, piperidine, and piperazine.

In many embodiments, chromonic compounds can be represented by one of the following structures:

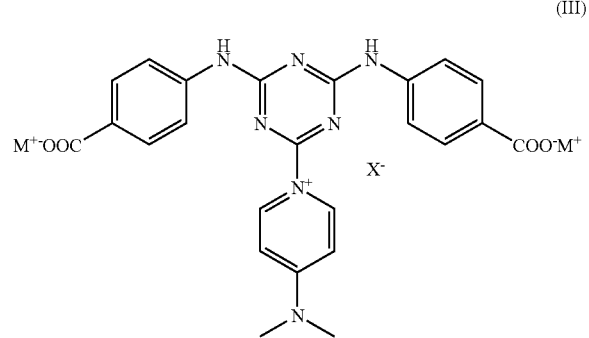

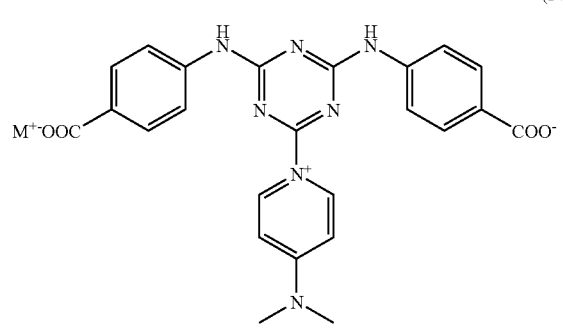

wherein $X^-$ is a counterion. In some embodiments, $X^-$ is selected from the group consisting of $HSO_4^-$, $Cl^-$, $CH_3COO^-$, and $CF_3COO^-$.

Formula IV depicts the compound in its zwitterionic form. The pyridine nitrogen therefore carries a positive charge and one of the carboxy functional groups carries a negative charge ($COO^-$).

The silver ion releasing chromonic materials can be prepared, for example, by starting with a chromonic starting compound represented by one of the following structures:

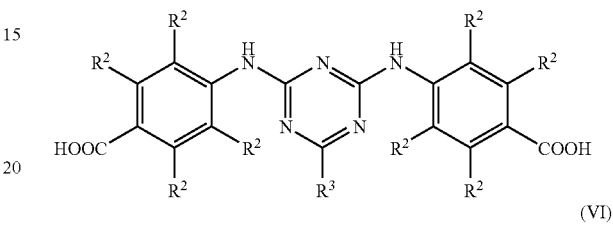

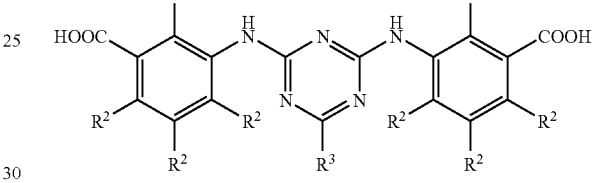

wherein $R^2$ is the same as described above.

As described in U.S. Pat. No. 5,948,487 (Sahouani et al.), which is herein incorporated by reference in its entirety, triazine derivatives such as the chromonic starting compound with formula V can be prepared as aqueous solutions. One synthetic route for the triazine molecules shown in formula V above involves a two-step process. Cyanuric chloride is treated with 4-aminobenzoic acid to give 4-{[4-(4-carboxyanilino)-6-chloro-1,3,5-triazin-2-yl]amino}benzoic acid. This intermediate is treated with a substituted or unsubstituted nitrogen-containing heterocycle. The nitrogen atom of the heterocycle displaces the chlorine atom on the triazine to form the corresponding chloride salt. The zwitterionic derivative can be prepared by dissolving the chloride salt in ammonium hydroxide and passing it down an anion exchange column to replace the chloride with hydroxide, (which deprotonates the carboxylic acid to yield a zwitterion) followed by solvent removal. Alternative structures, such as that shown in formula VI above, may be obtained by using 3-aminobenzoic acid instead of 4-aminobenzoic acid.

These chromonic starting compounds can be placed in aqueous solution, for example, at room temperature. Generally, the chromonic starting compound will be added to the solution to achieve a concentration in the range of about 5 to about 20 (or about 10) percent by weight of the solution. The chromonic starting compound in solution can then be mixed with an excess of silver ion source.

Examples of suitable silver ion sources include, for example, silver oxide, silver sulfate, silver acetate, silver chloride, silver lactate, silver phosphate, silver stearate, silver thiocyanate, silver proteinate, silver carbonate, silver nitrate, silver sulfadiazine, silver alginate, and combinations thereof. In many embodiments, the silver ion source includes silver salts such as, for example, silver carbonates, silver nitrates and silver acetates. In some embodiments, the silver ion source is a water soluble silver salt such as, for example, silver nitrate. Solubility of silver salts may be improved by addition of ammonia or ammonium salts, as is known in the art.

Examples of suitable concentrations of the silver ion source in the silver chromonic solution range from about 0.1% to about 15% by weight, based on the total weight of the silver chromonic solution. In some embodiments, concentrations of the silver ion source in the silver chromonic solution range from about 1% to about 5% by weight, based on the total weight of the silver chromonic solution.

With regards to silver oxide, a variety of valence states of the silver oxide may be used (e.g., where the oxidation state is silver (II) oxide or silver (III) oxide). The valence state of the silver oxide may be determined by depositing a silver oxide of a given valence state (e.g., $Ag_2O$, $AgO$, $Ag_2O_3$, $Ag_2O_4$). Alternatively, the valence state of the silver oxide may be increased by adding an oxidizing agent in the silver chromonic solution, or applying an oxidizing agent to the chromonic layer 120 after applying the silver chromonic solution to the article 100. Examples of suitable oxidizing agents include hydrogen peroxide, alkali metal persulfates, permanganates, hypochlorites, perchlorates, nitric acid, and combinations thereof. An example of a suitable alkali metal persulfate includes sodium persulfate as discussed in Antelman, U.S. Pat. No. 6,436,420, which is incorporated by reference in its entirety.

Precipitate can be filtered away to remove excess silver ion source metal, and then the resulting silver chromonic solution can be deposited (via contact and/or non-contact deposition techniques) on the articles, described herein, and then dried (for example, by air and then in an oven at around 70° C.) to yield the silver ion releasing chromonic material.

Silver ion releasing chromonic structures or particles can have any useful size. In many embodiments, the silver ion releasing chromonic materials have a mean diameter of less than one micrometer, or in a range from 1 to 500 nanometers, or in a range from 1 to 250 nanometers, or in a range from 1 to 100 nanometers, or in a range from 5 to 50 nanometers.

The silver ion releasing chromonic material 120 can be disposed adjacent to the substrate 110 via any useful method to form a layer, indicia, a pattern, and the like. In many embodiments, the adhesive layer 130 is a pressure sensitive adhesive layer and the silver ion releasing chromonic material 120 is disposed on at least a portion of the pressure sensitive adhesive layer 130. In some embodiments, the silver ion releasing chromonic material 120 can be disposed via contact deposition or non-contact deposition.

Suitable non-contact deposition techniques can be independent of the surface being coated. As such, a non-contact deposition mechanism may be moved in a transverse direction to the surface being coated, while imparting substantially no transverse force to the surface. In contrast to contact coating techniques, non-contact deposition allows the same processing equipment to be used for coating a variety of different surfaces without requiring changes in formulations or process parameters. Examples of suitable non-contact deposition techniques include inkjet printing, spray atomization deposition, electrostatic deposition, microdispensing, and mesoscale deposition. Particularly suitable non-contact deposition techniques include inkjet printing and spray atomization deposition.

Inkjet printing operates by ejecting a silver chromonic solution onto, for example, the adhesive layer 130 in controlled patterns of fluid droplets. Examples of suitable inkjet printing methods include thermal inkjet, continuous inkjet, piezo inkjet, bubble inkjet, drop-on-demand inkjet, and acoustic inkjet. Printheads for such printing methods are commercially available from Hewlett-Packard Corporation, Palo Alto, Calif. and Lexmark International, Lexington, Ky. (thermal inkjet); Domino Printing Sciences, Cambridge, UK (continuous inkjet); and Trident International, Brookfield, Conn., Epson, Torrance, Calif., Hitachi Data Systems Corporation, Santa Clara, Calif., Xaar PLC, Cambridge, UK, Spectra, Lebanon, N.H., and Idanit Technologies, Ltd., Rishon Le Zion, Israel (piezo inkjet). Examples of a suitable inkjet printhead models include the NOVA series such as the NOVA-Q printhead commercially available from Spectra Inc., and the XJ128 series such as the XJ128-200 printhead commercially available from Xaar PLC. When using the XJ128-200 printhead, the silver/chromonic solution may be coated on the adhesive layer 130 by piezoelectrically driving the printhead at 1.25 kilohertz (kHz) and 35 volts (V), with a printing resolution of 300×300 dots-per-inch (dpi). This generates drops with nominal volumes of about 70 picoliters (pL).

Inkjet printing also allows for the creation of silver ion releasing chromonic indicia 120 and/or graphics 120 on the substrate surface 112 and/or adhesive layer 130. As such, the pattern that the silver chromonic solution is inkjet printed onto the surface may also convey textual and graphical messages. In one embodiment, the messages may be visually observable through the use of pigments or dyes contained in the silver chromonic solution, which remain concentrated on or near the surface when the silver chromonic solution substantially dries. In many embodiments, the silver ion source itself provides coloration for the messages on the surface. For example, many silver-containing compounds, such as silver nitrate, are clear when in the fluid solution, but turn a dark brown color when dried (or reduced). This precludes the need for additional colorants to render the inkjet printed patterns visually observable. Examples of suitable messages include company logos, instructions for use of the article, brand names, and designs for aesthetic appearance.

Spray atomization deposition operates by emitting the silver chromonic solution through an air impingement nozzle or air stripping nozzle to atomize the silver chromonic solution to some degree. The atomized silver chromonic solution is then directed onto the adhesive layer 130 or substrate surface 112. An example of suitable spray atomization deposition systems include commercially available spray heads and bodies, such as those from Spraying Systems Co., Wheaton, Ill. The spray heads may also include fan spray adaptations to fan out the primary atomization sources for creating elliptical patterns. Suitable operating conditions include spraying the silver chromonic solution on the surface with a volumetric flow rate of about 5 milliliters/minute (mL/min), a web speed of about 15 feet/minute (about 4.6 meters/minute), an atomizer nozzle setting of about 23 pounds/inch$^2$ (psi) (about 159 kilopascals (kPa)), and a fan nozzle setting of about 20 psi (about 138 kPa). The spray heads generate droplets with diameters ranging from about 2 micrometers to about 20 micrometers.

The silver chromonic solution described herein desirably exhibits a sufficiently low viscosity to be coated by non-contact deposition. The desired viscosity will generally depend on the non-contact deposition technique used. For example, for inkjet printing, the silver chromonic solution desirably exhibits a viscosity below about 30 centipoise (i.e., 30 milliPascal-seconds), or below about 25 centipoise, or below about 20 centipoise at the desired inkjetting temperature (typically from about 25° C. to about 65° C.). However, the optimum viscosity characteristics for the silver chromonic solution will depend primarily upon the inkjetting temperature and the type of inkjet system used. For piezo inkjet applications, suitable viscosities for the silver chromonic solution range from about 3 to about 30 centipoise, or from about 10 to about 16 centipoise, at temperatures ranging from about 25° C. to about 65° C.

The biologically-active article 100 represents a suitable article that may be prepared with a silver ion releasing chromonic material 120. In many embodiments, the articles 100 are adhesive medical articles, such as adhesive wound dressings. Examples of suitable adhesive medical articles include adhesive wound dressings under the trade designation "TEGADERM" Dressings, which are commercially available from 3M Company, St. Paul, Minn.

The substrate 110 of the article 100 generally defines the bulk of the article 100 (e.g., a gauze bandage for a wound dressing). The optional adhesive layer 130 can be a layer of a pressure sensitive adhesive material disposed on the substrate surface 112 to adhere the article 100 to another surface such as, for example, the skin of a patient. The depicted layers are not to scale. In some embodiments the chromonic material layer 120 may be combined with the adhesive layer 130 so that the chromonic material is dispersed in the adhesive.

Examples of suitable materials for the substrate 100 include fabric, non-woven or woven polymeric webs, including those made by blown microfiber processes, knits, polymer films, hydrocolloids, foam, metallic foils, paper, gauze, natural or synthetic fibers, cotton, rayon, wool, hemp, jute, nylon, polyesters, polyacetates, polyacrylics, alginates, ethylene-propylene-diene rubbers, natural rubber, polyesters, polyisobutylenes, polyolefins (e.g., polypropylene polyethylene, ethylene propylene copolymers, and ethylene butylene copolymers), polyurethanes (including polyurethane foams), vinyls including polyvinylchloride and ethylene-vinyl acetate, polyamides, polystyrenes, fiberglass, ceramic fibers, elastomers, thermoplastic polymers, and combinations thereof. Such materials can be used as backing substrates in a variety of conventional medical products.

In many embodiments, the adhesive layer 130 is pressure sensitive adhesive (PSA). Examples of suitable materials for the adhesive layer 130 include PSAs based on acrylates, polyurethanes, silicones, rubber based adhesives (including natural rubber, polyisoprene, polyisobutylene, and butyl rubber), and combinations thereof. Examples of suitable acrylates include polymers of alkyl acrylate monomers such as methyl methacrylate, ethyl methacrylate, n-butyl methacrylate, methyl acrylate, ethyl acrylate, n-butyl acrylate, iso-octyl acrylate, iso-nonyl acrylate, 2-ethyl-hexyl acrylate, decyl acrylate, dodecyl acrylate, n-butyl acrylate, hexyl acrylate, and combinations thereof.

In some embodiments, materials for the adhesive layer 130 include silicone-based adhesives, which exhibit several beneficial properties over traditional PSAs used in wound care applications. For example, silicone-based adhesives may be formulated to offer good skin adhesion characteristics, offer excellent conformability, and provide a gentle release from the skin and wound site. Silicone-based adhesives can be formed from the reaction of a polysiloxane gum and a resin as a two-part system, one part hindered system to prevent premature reaction, or even as a hot melt system. Examples of suitable silicone-based adhesives include polydiorganosiloxane-based adhesives; adhesives commercially available under the trade designation "SILASTIC 7-6860" Biomedical Grade Adhesive from Dow Corning Corp., Midland, Mich.; adhesives disclosed in Sherman et al., U.S. Pat. No. 6,407,195, which is incorporated herein by reference; and combinations thereof.

The article 100 may also include a liner (not shown) that is disposed on at least a portion of the adhesive layer 130 and the silver ion releasing chromonic material 120, opposite the substrate 110, to protect the adhesive layer 130 prior to use. Liners, which are suitable for use with the article 100, may be made of materials such as kraft papers, polyethylene, polypropylene, polyester, and combinations thereof. The liners are preferably coated with compositions containing release agents, such as polymerized fluorochemicals or silicones. The low surface energy of the liner provides for an easy removal from the surface of the adhesive layer 130 without substantially affecting the biological active that is concentrated on or near the adhesive surface.

In some embodiments, the silver ion source can be reduced via reduction methods known in the art either before or after applying the silver chromonic solution to the article 100. For example, the reduction can be accomplished by using a reducing agent (for example, tris(dimethylamino)borane, sodium borohydride, potassium borohydride, or ammonium borohydride), electron beam (e-beam) processing, or ultraviolet (UV) light.

The silver ion releasing chromonic layer 120 can be dried either before or after the reduction step. Drying of the coated article 100 can be achieved using any means suitable for drying aqueous coatings. Useful drying methods will not damage the coating or significantly disrupt the orientation of the coated silver ion releasing chromonic layer 120 imparted during coating or application.

As described above, in many embodiments, the silver ion source 122 provides coloration for the messages on the article 100. For example, many silver-containing compounds, such as silver nitrate, are clear when in the fluid solution, but turn a dark brown color when dried (or reduced). As the silver ions are released from the article 100, the coloration of the message, indicia, and/or pattern fades. Thus, a user is able to determine when the silver ion-releasing article is no longer releasing silver ions (often termed an "end of life" indicator.).

EXAMPLES

The present invention should not be considered limited to the particular examples described herein, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

As used herein,

"PET" refers to poly(ethylene terephthalate) film having a thickness of approximately 102 micrometers (0.004 inch), available from Mitsubishi Polyester Corp., Tokyo, Japan;

"TEGADERM" refers to an adhesive wound dressing, manufactured by 3M Company, St. Paul, Minn.;

"PAPER-BACKED TEGADERM" refers to a paper-backed adhesive wound dressing, manufactured by 3M Company, St. Paul, Minn.;

"PVA FILM" refers to a poly(vinyl alcohol) film having a thickness of approximately 40 micrometers (0.0016 inch), available from Mitsui Plastics Inc., White Plains, N.Y.;

"TIPS FILM" refers to a microporous polypropylene membrane, prepared as described in U.S. Pat. Nos. 4,726,989 and 5,120,594;

"MPS FILM" refers to a polypropylene nonwoven, prepared as described in U.S. Pat. No. 6,110,588;

"SPUNBOND" refers to spunbond polypropylene, available from Hanes Companies, Inc., Conover, N.C.);

"GAUZE" refers to cotton nonwoven gauze, available from American Fiber & Finishing, Inc., Albemarle, N.C.;

"FOAM" refers to a non-adhesive foam wound dressing (believed to be a polyurethane open-cell foam), obtained as Product Number 90-601 from 3M Company, St. Paul, Minn.;

"PP NONWOVEN" refers to a polypropylene blown microfiber nonwoven.

Zones of Inhibition Test

Antimicrobial activity of the substrates comprising a silver ion releasing chromonic material (the biologically active articles) was evaluated using the zones of inhibition test. A solution of *Staphylococcus aureus* (A.T.C.C. 25923) was prepared at a concentration of $1 \times 10^8$ colony forming units (CFU) per milliliter in phosphate buffered saline (PBS) using a 0.5 McFarland Equivalence Turbidity Standard. Bacterial lawns were prepared by dipping a sterile cotton applicator into the solution and swabbing a dry surface of a trypticase soy agar plate in three different directions. Three 7-millimeter diameter discs for each sample were wetted with PBS and were then placed onto the plate and were pressed firmly against the agar with sterile forceps to ensure contact with the agar. The plate was held in a refrigerator at 4° C. for three hours and was then incubated at 36° C. for 24 hours, after which time the plates were examined for inhibition of the growth of *S. aureus*. The primary zone of inhibition was determined by measuring the diameter of the area under and around the disks on the agar plate in which growth of *S. aureus* was substantially entirely inhibited (the primary zone of inhibition). The secondary zone of inhibition was determined by measuring the diameter of the area across the disks on the agar plate in which growth of the *S. aureus* was partially inhibited. The value of the primary and secondary zones of inhibition is reported below as the diameter (in millimeters) of each zone, including the area under the 7-mm diameter sample disk.

Ink Jet Printing

Ink Jet Printing of substrates was carried out using a Model XJ128-200 piezoelectric printhead, manufactured by Xaar PLC, Cambridge, United Kingdom, having a nominal drop volume of 70 picoliters and a printing resolution of 300 by 300 dpi (dots per inch). The printhead was driven at 1250 Hz and 35 V. The print resolution of 300 by 300 dpi provided, at 100% substrate surface coverage, 90,000 drops (300×300) per square inch. Lesser substrate surface coverage was obtained by depositing fewer drops per square inch. Thus, 30% substrate surface coverage resulted from depositing 27,000 drops per square inch.

Adhesion Measurements

The adhesive strength of the adhesive articles prepared in the Examples were determined according to the ASTM D3330 using a Thwing-Albert Tensile Tester, obtained from Thwing-Albert Instrument Co., Philadelphia, Pa. The test surface consisted of a #302 AISI stainless steel annealed surface, which was cleaned with a mixture of equal parts by weight of isopropanol and heptane. The samples were pulled at a 180° angle with a crosshead speed of 300 millimeters per minute and a gauge length 125 millimeters. The adhesive strength reported in the Examples was the average of six measurements.

Preparative Example 1

Preparation of a Silver Chromonic Solution

A mixture of the chromonic compound of Formula V (1.0 g), deionized water (4.0 g) and ethanolamine (0.16 g) was stirred together for approximately two hours. To this stirring solution there was added a solution prepared by combining deionized water (4.0 g) silver nitrate (0.4 g) and ethanolamine (0.53 g). The resultant mixture was stirred for approximately thirty minutes to afford the silver chromonic solution.

Example 1

Preparation of a PET Biologically Active Article

The silver chromonic solution of Preparative Example 1 was coated onto a sheet of PET using a notched coating bar. The wet coating thickness was approximately 8 micrometers (0.0003 inch). The coating was dried using a heat gun. The coated sheet was then exposed to tris(dimethylamino)borane vapor by placing it in a sealed glass jar with the borane for five minutes. The primary zone of inhibition was determined to be 12 millimeters.

Examples 2-9

Preparation of Biologically Active Articles by Ink Jet Printing

One part by weight of the silver chromonic solution of Preparative Example 1 was mixed with three parts by weight of deionized water. This mixture was ink jet printed on the substrates listed in Table 1 at 100% substrate surface coverage. Three disks of each printed substrate, each having a diameter of seven millimeters, were evaluated using the zones of inhibition test described above. The data are given in Table 1. In table 1, "ZOI" means zone of inhibition. The adhesive strength of the inkjet printed TEGADERM film was evaluated as described above and was found to be 160.7+/−11.5 grams per centimeter (14.40+/−1.03 ounces per inch).

TABLE 1

Zone of Inhibition Data for Examples 2-9

| Example | Substrate | Primary ZOI (mm) | Secondary ZOI (mm) |
|---|---|---|---|
| 2 | TEGADERM | 7 | 10 |
| 3 | GAUZE | 11 | 12 |
| 4 | PVA FILM | 7 | 11 |
| 5 | TIPS FILM | 10 | 0 |
| 6 | MPS FILM | 0 | 9 |
| 7 | SPUNBOND | 11 | 13 |
| 8 | FOAM | 9 | 12 |
| 9 | PP NONWOVEN | 7 | 9 |

Example 10

Articles Having Time Dependent Biological Activity

One part by weight of the silver chromonic solution of Preparative Example 1 was mixed with three parts by weight of deionized water. One milliliter of this mixture was applied to a 51 millimeter by 51 millimeter (2 inches by 2 inches) sample of gauze. The gauze was then dried in a forced air oven at 80° C. for ten minutes. The dried gauze was then exposed to tris(dimethylamino)borane vapor by placing it in a sealed glass jar with the borane for ten minutes. Three disks of the treated gauze, each having a diameter of seven millimeters, were evaluated using the zones of inhibition test for 24 hours. After noting the results, each of the disks was removed from the agar plate (under aseptic conditions) and was placed on a second agar plate on which was growing active colonies of *S. aureus*. This second plate was then incubated for 24 hours and the zones of inhibition were then noted. Each of the disks was removed from the second agar plate (under aseptic conditions) and was placed on a third agar plate on which was growing active colonies of S. aureus. This third plate was then incubated for 24 hours and the zones of inhibition were then noted. The zones of inhibition after the first day on the first plate, after the second day on the second plate, and after the third day on the third plate (the time dependent zones of inhibition data) are given in Table 2 for Day 1, Day 2, and Day 3, respectively.

TABLE 2

Time Dependent Zones of Inhibition Data for Example 10

| Day | Primary ZOI (mm) | Secondary ZOI (mm) |
|---|---|---|
| Day 1 | 11 | 12 |
| Day 2 | 8 | 9 |
| Day 3 | 0 | 8 |

Examples 11-12

Preparation of Biologically Active Articles by Spray Coating

One part by weight of the silver chromonic solution of Preparative Example 1 was mixed with two parts by weight of deionized water. This mixture was spray coated onto a web of paper-backed TEGADERM (Example 11) and onto a web of PET (Example 12) using a spray/atomizer nozzle that generated droplets having a range of diameters of approximately two micrometers to approximately twenty micrometers. The spray flow rate was approximately 20 milliliters per minute and the web speed was approximately 4.6 meters (approximately 15 feet) per minute. The coated films were dried in a forced air oven at approximately 150° C. for ten minutes. The coated films were then exposed to tris(dimethylamino)borane vapor by placing them in sealed glass jars with the borane for five minutes. The antimicrobial activity of each spray-coated film was evaluated using the zones of inhibition test described above. In Example 11, the paper-backed TEGADERM exhibited a primary zone of inhibition of 10 millimeters and a secondary zone of inhibition of 12 millimeters. In Example 12, the PET exhibited a primary zone of inhibition of 11 millimeters and a secondary zone of inhibition of 13 millimeters.

The adhesive strength of the inkjet printed paper-backed TEGADERM film was evaluated as described above and was found to be 131.6+/−10.4 grams per centimeter (11.79+/−0.93 ounces per inch).

Comparative Example 1

Zones of Inhibition Data for TEGADERM

The antimicrobial activity of three seven-millimeter diameter disks of TEGADERM (not treated with a silver chromonic mixture) was evaluated using the zones of inhibition test described above. The primary and secondary zones of inhibition were both zero. The adhesive strength of this TEGADERM film (not treated with a silver chromonic mixture) was evaluated as described above and was found to be 160.5+/−15.7 grams per centimeter (11.79+/−0.93 ounces per inch).

What is claimed is:

1. A wound dressing comprising a biologically-active article, the biologically-active article comprising a substrate having a substrate surface, and a silver ion releasing chromonic material disposed adjacent to the substrate surface, wherein the silver ion releasing chromonic material comprising a chromonic compound and a silver ion source, wherein the silver ion source is an antimicrobial agent, wherein the release of silver ions from the silver ion source is moisture activated, and wherein the silver ion releasing chromonic materials is represented at least one of the following general structures:

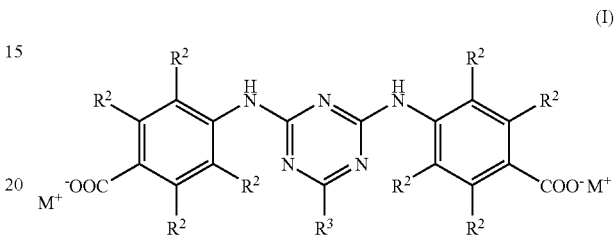

wherein for structure I, each $R^2$ is independently selected from the group consisting of electron donating groups, electron withdrawing groups, and electron neutral groups; $R^3$ is selected from the group consisting of substituted and unsubstituted heteroaromatic rings and substituted and unsubstituted heterocyclic rings, these rings being linked to the triazine group through a nitrogen atom within the ring of $R^3$, and $M^+$ is a silver metal cation;

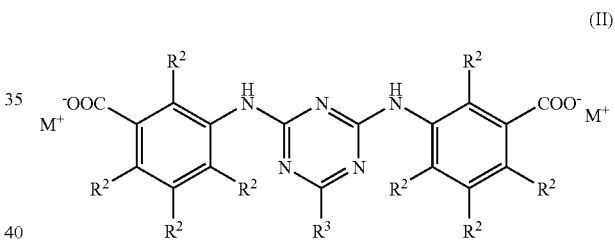

wherein for structure II, each $R^2$ is independently selected from the group consisting of electron donating groups, electron withdrawing groups, and electron neutral groups; $R^3$ is selected from the group consisting of substituted and unsubstituted heteroaromatic rings and substituted and unsubstituted heterocyclic rings, these rings being linked to the triazine group through a nitrogen atom within the ring of $R^3$; and $M^+$ is a silver metal cation;

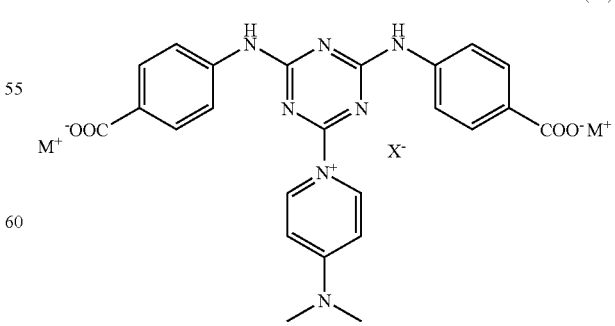

wherein for structure III, $M^+$ is a silver metal cation; and $X^-$ is a counterion; and

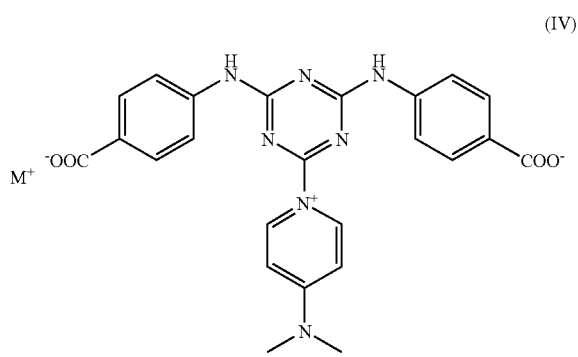
(IV)

wherein for structure IV, M⁺ is a silver metal cation.

2. The wound dressing according to claim 1, wherein in structure (III), $X^-$ is selected from the group consisting of $HSO_4^-$, $Cl^-$, $CH_3COO^-$, and $CF_3COO^-$.

3. The wound dressing according to claim 1 wherein the silver ion releasing chromonic material forms indicia.

4. The wound dressing according to claim 1 wherein the silver ion releasing chromonic material is in the form of a pattern.

5. The wound dressing according to claim 4 wherein the pattern of silver ion releasing chromonic material is a printed pattern on the surface of the article.

6. The wound dressing according to claim 1 wherein the silver ion source has a mean diameter in a range from 1 to 500 nanometers.

7. The wound dressing according to claim 1 wherein the chromonic compound has a chromonic structure that encapsulates the silver ion source and provides controlled release of silver ions from the chromonic structure.

8. The wound dressing according to claim 1 wherein the chromonic compound has a chromonic structure that forms cavities, and the silver ion source is disposed in the cavities.

9. The wound dressing according to claim 1 wherein the chromonic compound exhibits a self-assembling stacking structure of chromonic molecules that form cavities, and the silver ion source is intercalated into the cavities.

10. The wound dressing according to claim 1 wherein the release of silver ions from the silver ion source is a time dependent controlled release of silver ions.

11. A wound dressing according to claim 1 wherein the release of silver ions from the silver ion source is sustainable over time so as to provide antimicrobial activity suitable for the treatment of chronic wounds.

12. The wound dressing according to claim 1 wherein the silver ion releasing chromonic material exhibits a visible coloration that fades as silver ions are released from the silver ion source.

13. The wound dressing according to claim 12 wherein the visible coloration of the silver ion releasing chromonic material fades such that a user is able to determine when the silver ions are no longer being released.

* * * * *